United States Patent
Schmidt et al.

(10) Patent No.: US 12,213,749 B2
(45) Date of Patent: Feb. 4, 2025

(54) MEDICAL OBJECT FOR ARRANGEMENT IN AN OBJECT UNDER EXAMINATION AND SYSTEM FOR SENSING A MEDICAL OBJECT

(71) Applicant: Siemens Healthcare GmbH, Erlangen (DE)

(72) Inventors: Oliver Schmidt, Erlangen (DE); Martin Ostermeier, Buckenhof (DE); Sandro Francesco Tedde, Weisendorf (DE); Stephan Kellnberger, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 169 days.

(21) Appl. No.: 17/746,941

(22) Filed: May 17, 2022

(65) Prior Publication Data
US 2022/0370148 A1    Nov. 24, 2022

(30) Foreign Application Priority Data
May 19, 2021    (DE) .................. 10 2021 205 113.8

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0095* (2013.01); *A61B 5/6852* (2013.01);
(Continued)

(58) Field of Classification Search
CPC .... A61B 2034/2063; A61B 2034/2061; A61B 8/0841; A61B 34/20; A61B 34/10;
(Continued)

(56) References Cited

U.S. PATENT DOCUMENTS

| 8,839,672 B2 | 9/2014 | Emelianov et al. |
| 2004/0131299 A1* | 7/2004 | Adoram ............... A61B 5/6852 385/12 |

(Continued)

FOREIGN PATENT DOCUMENTS

| WO | WO-0155689 A1 * | 8/2001 | ............ G01M 11/00 |
| WO | WO-2006061829 A1 * | 6/2006 | ........... A61B 5/0084 |

(Continued)

OTHER PUBLICATIONS

Guo, Xiaoyu, et al. "Active ultrasound pattern injection system (AUSPIS) for interventional tool guidance." PloS one 9.10 (2014): e104262. pp. 1-13.
(Continued)

*Primary Examiner* — Peter Luong
(74) *Attorney, Agent, or Firm* — Lempia Summerfield Katz LLC

(57) ABSTRACT

A medical object for arrangement in an object under examination includes an optical fiber. The optical fiber is configured to contact at least one light source optically. The medical object further includes multiple photoacoustic absorbers that are arranged in sections along a direction of longitudinal extension of the optical fiber and/or along a periphery of the medical object. The multiple photoacoustic absorbers are configured to be arranged at least in part in the object under examination. The optical fiber is configured to conduct an excitation light emitted by the at least one light source to the multiple photoacoustic absorbers. The multiple photoacoustic absorbers are configured to be excited by the excitation light for the photoacoustic emission of ultrasound.

14 Claims, 8 Drawing Sheets

(51) Int. Cl.
*A61B 8/08* (2006.01)
*A61B 34/10* (2016.01)
*A61B 90/00* (2016.01)
*G01S 15/89* (2006.01)

(52) U.S. Cl.
CPC ............ *A61B 8/0841* (2013.01); *A61B 34/10* (2016.02); *G01S 15/8965* (2013.01); *A61B 2034/105* (2016.02); *A61B 2034/2061* (2016.02); *A61B 2034/2063* (2016.02); *A61B 2090/3929* (2016.02)

(58) Field of Classification Search
CPC ..... A61B 5/0095; A61B 5/6852; A61B 5/061; A61B 2034/105; A61B 2034/2046; A61B 2090/3929; A61B 2090/376; A61B 2090/3788; G01S 15/8965
See application file for complete search history.

(56) References Cited

U.S. PATENT DOCUMENTS

2006/0241572 A1 10/2006 Zhou
2010/0087732 A1* 4/2010 Eberle .................... A61B 8/12
  600/437
2013/0319123 A1 12/2013 Wang et al.
2018/0310831 A1 11/2018 Cheng et al.
2021/0369352 A1* 12/2021 Takeshima ........... A61B 8/4245
2023/0372024 A1* 11/2023 Frushour ................ A61B 34/20

FOREIGN PATENT DOCUMENTS

WO   2008066962 A1   6/2008
WO   2017079732 A1   5/2017

OTHER PUBLICATIONS

Guo, Xiaoyu, et al. "Photoacoustic active ultrasound element for catheter tracking." Photons Plus Ultrasound: Imaging and Sensing 2014. vol. 8943. International Society for Optics and Photonics, 2014. pp. 1-7.

Tian, Jiajun, Qi Zhang, and Ming Han. "Distributed fiber-optic laser-ultrasound generation based on ghost-mode of ilted fiber Bragg gratings." Optics express 21.5 (2013): 6109-6114.

* cited by examiner

MEDICAL OBJECT FOR ARRANGEMENT IN AN OBJECT UNDER EXAMINATION AND SYSTEM FOR SENSING A MEDICAL OBJECT

This application claims the benefit of German Patent Application No. DE 10 2021 205 113.8, filed on May 19, 2021, which is hereby incorporated by reference in its entirety.

BACKGROUND

The present embodiments relate to a medical object for arrangement in an object under examination and a system for sensing a medical object.

Endovascular procedures may normally be monitored using X-ray devices (e.g., angiography X-ray devices) that, using X-ray radiation, may map a medical object (e.g., a guide wire and/or a catheter) and an anatomy of an object under examination. Navigation within the anatomy of the object under examination often proves difficult in this case, since in a two-dimensional (2D) X-ray image, there is a lack of depth information. The same applies for a merger of intraoperative 2D X-ray images with a preoperative image dataset (e.g., a volume dataset) that was recorded, for example, by a computed tomography system and/or a magnetic resonance system, since a 2D/3D registration is often necessary here. A biplane X-ray system is capable of solving this problem in part, but is very complex and in general is rarely available. Further, a high X-ray dose throughout the procedure and a repeated administration of contrast agents is often detrimental.

Low-radiation or radiation-free continuous sensing of a shape of the medical object may be enabled by shape sensing technology. For this, the medical object may have an optical fiber with a fiber Bragg grating (FBG) as a shape sensing sensor, where the shape (e.g., the current shape) of the optical fiber may be sensed using a quantity of light reflected by the fiber Bragg grating. Further, by merging the preoperative image data with the sensed shape of the medical object, a "virtual navigation" of the medical object may be implemented. In this case, a spatial positioning (e.g., a current spatial positioning) of the medical object may be determined with a high readout frequency and may be inserted virtually into the preoperative image data and/or the intraoperative 2D X-ray image. The intraoperative 2D X-ray image is then to be refreshed only very infrequently. As a result of this, the X-ray dose may be reduced. A disadvantage of this, however, is that a registration between a coordinate system of the shape sensing sensor with the preoperative image data and/or the intraoperative 2D X-ray image is to be provided. Further, the shape sensing technology often exhibits a high degree of inaccuracy, since a coordinate origin of a coordinate system of the shape sensing sensor may lie outside the object under examination.

A further possibility for sensing a medical object is based on electromagnetic beacons. However, additional hardware and/or a complex calibration procedure is often to be provided for this in order to register a coordinate system of the electromagnetic system for sensing the beacon with a coordinate system of the object under examination.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a spatial progression of a medical object may be sensed precisely.

A first aspect of the present embodiments relates to a medical object for arrangement in an object under examination. The medical object has an optical fiber. In this case, the optical fiber is configured to contact at least one light source optically. Further, the medical object has multiple photoacoustic absorbers that are arranged in sections along a direction of longitudinal extension of the optical fiber and/or along a periphery of the medical object. Further, the multiple photoacoustic absorbers are configured to be arranged at least in part in an object under examination. Further, the optical fiber is configured to conduct an excitation light emitted by the at least one light source to the multiple photoacoustic absorbers. In this case, the multiple photoacoustic absorbers are configured to be excited by the excitation light for the photoacoustic emission of ultrasound.

The at least one light source may, for example, have a light-emitting diode (LED) and/or a laser (e.g., a short-pulse laser) that is configured for the generation and/or emission (e.g., the pulsed generation and/or emission) of the excitation light having a defined wavelength and/or a defined wavelength range and/or a defined intensity modulation and/or a defined pulse frequency and/or a defined pulse duration. In this case, the defined wavelength and/or the defined wavelength range and/or the defined intensity modulation and/or the defined pulse frequency and/or the defined pulse duration may be adjustable and/or predefinable by a user (e.g., by an input by the user using an input unit). For example, the excitation light may have at least one narrowband and/or broadband wavelength range (e.g., in an infrared range and/or near infrared range). Further, the excitation light may be configured to be multispectral. The at least one light source may be configured to generate the excitation light such that the multiple photoacoustic absorbers are excited for the photoacoustic emission of the ultrasound. For example, the at least one light source may be configured to generate the excitation light with the defined wavelength and/or within the defined wavelength range. The defined wavelength and/or the defined wavelength range corresponds at least in part to an absorption spectrum (e.g., an absorption wavelength and/or an absorption wavelength range) of the photoacoustic absorber. Further, the at least one light source may be configured for the pulsed emission of the excitation light (e.g., as flashes of light). As a result, the multiple photoacoustic absorbers may be illuminated in a pulsed manner by the excitation light and may be excited in accordance with their excitation sensitivity for the photoacoustic emission of the ultrasound.

The medical object may be configured as an instrument (e.g., an elongated, diagnostic and/or surgical instrument; as a catheter and/or endoscope and/or guide wire). Further, the medical object may have the optical fiber. The optical fiber may be arranged along a direction of longitudinal extension of the medical object.

The optical fiber may, for example, be configured as an optical waveguide. Further, the optical fiber may be a glass fiber and/or a polymer optical fiber (e.g., a fiber strand). The at least one light source may be configured to feed the excitation light into the optical fiber via the optical contacting (e.g., at a proximal section of the medical object). The medical object (e.g., the optical fiber) may, at least in sections, be configured to be flexible (e.g., bendable) and/or rigid.

The medical object may further have the multiple photoacoustic absorbers (e.g., on a distal section of the optical fiber and/or of the medical object). In this case, the optical fiber may be configured to conduct the excitation light that is emitted by the at least one light source and is fed into the optical fiber by the optical contacting, to the multiple photoacoustic absorbers. The multiple photoacoustic absorbers (e.g., the medical object) may be configured to be arranged, at least in part, in the object under examination (e.g., in a hollow organ of the object under examination). In this case, the at least one light source may be configured to be arranged intracorporeally or extracorporeally. Further, the object under examination may be a human and/or animal patient. Further, the hollow organ may, for example, be a section of a vessel (e.g., a vein and/or artery and/or aorta), and/or a liver and/or a lung and/or a section of intestine.

The multiple photoacoustic absorbers may be configured at least in part (e.g., completely) to be identical or different from one another (e.g., with respect to excitation sensitivities, such as an absorption spectrum and/or or an absorption rate, and/or with respect to shape and/or spatial extent). Further, the multiple photoacoustic absorbers may at least in part (e.g., completely) differ with respect to the ultrasound emitted in each case (e.g., an ultrasound intensity and/or ultrasound wavelength and/or an ultrasound wavelength range). As a result, the multiple photoacoustic absorbers may at least in part (e.g., completely) be identifiable using the detected ultrasound. Further, the multiple photoacoustic absorbers may be arranged in sections (e.g., in each case in strips and/or in rings and/or in spirals) along the direction of longitudinal extension of the optical fiber. In this case, the multiple photoacoustic absorbers may be spaced apart from one another along the direction of longitudinal extension of the optical fiber and/or may be adjacent to one another and/or at least in part overlapping. Alternatively or additionally, the multiple photoacoustic absorbers may be arranged in sections along a periphery (e.g., a radial periphery) of the medical object. For example, the periphery of the medical object may include multiple radial sectors that are arranged spaced apart from one another or adjacent to one another. The multiple photoacoustic absorbers may in each case be arranged in one of the radial sectors of the medical object. The multiple photoacoustic absorbers may be arranged on an external surface of the medical object. The multiple photoacoustic absorbers may have a defined spatial arrangement along the direction of longitudinal extension of the optical fiber and/or along the periphery of the medical object (e.g., a strip pattern and/or a spiral pattern). The optical fiber may be configured to be substantially cylindrical along a direction of longitudinal extension. Further, the optical fiber may have, at least in sections, a sheathing that is configured to prevent an escape of the excitation light as a result of the excitation light being reflected off a boundary surface between a core region of the optical fiber and the sheathing. In this case, the sheathing may have a lower refractive index compared to the core region. For the excitation light to be coupled out of the optical fiber at least in sections, the multiple photoacoustic absorbers may optically contact the core region of the optical fiber. For this, the sheathing of the optical fiber may be omitted (e.g., interrupted) on sections along the direction of longitudinal extension of the optical fiber and/or on sections along a periphery of the medical object (e.g., the optical fiber), on which the multiple photoacoustic absorbers are arranged. Alternatively or additionally, the optical fiber (e.g., the core region and/or the sheathing) may be doped with microstructures on the sections on which the multiple photoacoustic absorbers are arranged. As a result, the excitation light may be coupled out from the core region of the optical fiber and coupled into the multiple photoacoustic absorbers. Further, the multiple photoacoustic absorbers may, for example, be attached in sections as a coating to the optical fiber (e.g., the core region and/or the sheathing). In this case, the optical fiber (e.g., the doping) may be configured such that in each case a defined (e.g., identical) portion of the excitation light is coupled out to the multiple photoacoustic absorbers. For this, the doping (e.g., the microstructures) may be arranged such that a further defined portion of the excitation light may pass (e.g., unhindered) the sections of the doping along the direction of longitudinal extension of the optical fiber. The doping (e.g., the microstructures) may, for example, be arranged in an edge region of the core region and/or an interior region of the sheathing. Further, the doping (e.g., the microstructures) may have a spatial arrangement optimized for coupling out the excitation light.

The multiple photoacoustic absorbers may in each case be configured to absorb at least part of the excitation light and to convert the excitation light into thermal energy. This may result in a reversible volume expansion of the photoacoustic absorbers. Thanks to the illumination (e.g., the pulsed illumination) of the photoacoustic absorbers with the excitation light, the photoacoustic absorbers may be excited to generate pressure variations that are emitted as the ultrasound. The excitation light may be configured to excite the multiple photoacoustic absorbers (e.g., selectively or non-selectively) for the photoacoustic emission of the ultrasound (e.g., sequentially or simultaneously).

Thanks to the arrangement of the multiple photoacoustic absorbers in sections along the direction of longitudinal extension of the optical fiber (e.g., of the medical object), the ultrasound may be emitted along this direction of longitudinal extension (e.g., radially). Thanks to the ultrasound being detected, the spatial progression of the medical object (e.g., of the optical fiber) may be sensed.

Alternatively or additionally, thanks to the arrangement of the multiple photoacoustic absorbers in sections along the periphery of the medical object, the ultrasound may be emitted radially (e.g., in the sectors of the periphery of the medical object). As a result, an orientation and/or torsion of the medical object may be sensed with respect to the direction of longitudinal extension of the medical object using the detected ultrasound.

This embodiment may also permit an especially space-saving and/or energy-efficient design of the medical object.

In a further form of embodiment of the medical object, the multiple photoacoustic absorbers may at least in part have different excitation sensitivities for the photoacoustic emission of the ultrasound.

The multiple photoacoustic absorbers may at least in part have different excitation sensitivities for the photoacoustic emission of the ultrasound (e.g., at least in part different excitation spectra, such as absorption wavelengths and/or absorption wavelength ranges, and/or activation energies, such as thermal activation energies). As a result, the multiple photoacoustic absorbers may be configured to be excited selectively by the excitation light at least in part (e.g., completely) for the photoacoustic emission of the ultrasound. Alternatively, the multiple photoacoustic absorbers may be configured to be excited non-selectively (e.g., simultaneously) by the excitation light for the photoacoustic emission of the ultrasound. In both cases, the ultrasound emitted by the individual photoacoustic absorbers may differ at least in part (e.g., in an ultrasound intensity and/or ultrasound wavelength and/or an ultrasound wavelength range). As a result, the emitted ultrasound may have a modulation (e.g., a superimposition of ultrasound waves that are emitted by the individual photoacoustic absorbers).

As a result, an identification (e.g., localization) of individual photoacoustic absorbers may also be enabled along the direction of longitudinal extension of the optical fiber (e.g., of the medical object) and/or along the periphery of the medical object using the emitted ultrasound.

In a further form of embodiment of the medical object, the optical fiber may have multiple core regions that run along the direction of longitudinal extension of the optical fiber. In this case, the multiple core regions may be configured to contact a light source optically in each case. Further, the medical object may have a sector along a periphery of the medical object that is in each case radial to the multiple core regions. In this case, the multiple photoacoustic absorbers may each be arranged in one of the radial sectors of the medical object and may each contact one of the core regions optically. Further, the core regions may be configured to conduct the excitation light emitted by the in each case optically contacted light source to the multiple photoacoustic absorbers.

The multiple core regions may run along the direction of longitudinal extension of the optical fiber (e.g., in parallel with one another). Further, the optical fiber may at least in sections have the sheathing that sheathes the multiple core regions at least in part. The sheathing may hold the multiple core regions in a defined arrangement (e.g., spaced apart from one another) along the direction of longitudinal extension of the optical fiber. Further, the sheathing may be configured to prevent an escape of the excitation light from the multiple core regions by the excitation light being reflected off the boundary surfaces of the core regions with the sheathing.

The multiple core regions may be configured to contact a light source optically in each case. For example, one of the multiple core regions may in each case contact one of the multiple light sources optically. In this case, the light source optically contacted by the respective core region may be configured to feed the excitation light into the core region (e.g., on a proximal section of the medical object).

The medical object may have a sector (e.g., an angular range) that is in each case radial to the multiple core regions along a periphery of the medical object. In this case, the periphery of the medical object may describe a periphery of a cross-sectional surface of the medical object that is substantially perpendicular to the direction of longitudinal extension of the medical object. Further, the radial sectors (e.g., the angular ranges) may be spaced apart from one another (e.g., delimited from one another by the sheathing) or may be arranged adjoining one another. The radial sectors may further have a spatial extension along the direction of longitudinal extension of the medical object.

The multiple photoacoustic absorbers may in each case be arranged in one of the radial sectors of the medical object and in each case contact one of the core regions optically. For this, the sheathing of the optical fiber on the radial sectors of the medical object on which the multiple photoacoustic absorbers are arranged may be omitted (e.g., interrupted). Alternatively or additionally, the optical fiber (e.g., the respective core region and/or the sheathing) on the radial sectors on which the multiple photoacoustic absorbers are arranged may be doped with microstructures. As a result, the excitation light may be coupled out from the core regions and coupled into the photoacoustic absorbers.

Because the core regions each contact a light source and each contact at least one of the multiple photoacoustic absorbers optically, the multiple photoacoustic absorbers may be selectively excited for the photoacoustic emission of the ultrasound. As a result, an orientation and/or torsion of the medical object with respect to the direction of longitudinal extension may be sensed using the detected ultrasound.

In a further form of embodiment of the medical object, the optical fiber (e.g., the core region of the optical fiber) may have a fiber Bragg grating. Providing the optical fiber has multiple core regions, the multiple core regions may each have a fiber Bragg grating. In this case, the fiber Bragg grating may have a periodic arrangement of sections along the direction of longitudinal extension of the optical fiber. Adjacent sections have different refractive indices in each case. In this case, the multiple photoacoustic absorbers may be arranged in sections along the direction of longitudinal extension of the optical fiber on one of the sections of the fiber Bragg grating in each case. Further, the fiber Bragg grating may be configured to filter the excitation light in the sections (e.g., differently). Further, the filtered excitation light may be configured to excite the multiple photoacoustic absorbers for the modulated emission of the ultrasound.

The fiber Bragg grating may be configured as an optical interference filter that is configured to reflect a portion of the excitation light. The portion has a wavelength within a filter wavelength range (e.g., a filter bandwidth) around a filter wavelength (e.g., the Bragg wavelength). In this case, a portion of the excitation light may in each case be reflected off the boundary surfaces between two adjacent sections of the fiber Bragg grating with different refractive indices. The Bragg wavelength may be determined by a grating period of the fiber Bragg grating (e.g., the periodic structure in the core region of the optical fiber) and the respective refractive indices. In this case, the periodic structure of the fiber Bragg grating may cause interference between the portions of the excitation light that are reflected off the periodic boundary surfaces. In the event of a deformation of the medical object (e.g., of the optical fiber), the result may be an expansion and/or compression, at least in sections, of the periodic structure. The result may be a change in the grating period of the fiber Bragg grating (e.g., a change in the filtering of the excitation light in the respective section). For example, a change may occur in a wavelength and/or a wavelength range of the reflected portion of the excitation light in the respective section. Further, in the event of the deformation of the optical fiber (e.g., because of photoelastic effects in the core region of the optical fiber), this may result in a change in the refractive indices.

Thanks to the differently filtered excitation light in the periodic sections of the fiber Bragg grating, the multiple photoacoustic absorbers may, as a function of respective arrangement on one of the sections, be excited differently for the emission of the ultrasound. As a result, the ultrasound emitted by the multiple photoacoustic absorbers in each case may differ (e.g., in the ultrasound intensity and/or the ultrasound wavelength and/or the ultrasound wavelength range). For example, the emitted ultrasound may be a function of the arrangement of the respective photoacoustic absorber along the direction of longitudinal extension of the optical fiber (e.g., the respective section of the fiber Bragg grating). As a result, the spatial positioning (e.g., position and/or orientation) of the individual photoacoustic absorbers of the medical object may be determinable as regards the direction of longitudinal extension of the medical object using the detected ultrasound.

A second aspect of the present embodiments relates to a system for sensing a medical object. In this case, the system has a medical object, a processing unit, at least one light source (e.g., multiple light sources), and an ultrasound unit. The at least one light source is configured to emit the excitation light. In this case, the excitation light is configured to excite the multiple photoacoustic absorbers for the photoacoustic emission of the ultrasound. Further, the ultrasound unit is configured to be arranged extracorporeally on a surface of the object under examination. Further, the ultrasound unit is configured for the detection of the ultrasound. Further, the processing unit is configured to determine a spatial progression of the medical object using the detected ultrasound. In an operating state of the system, the optical fiber optically contacts the at least one light source. Further, in the operating state of the system, the multiple photoacoustic absorbers are arranged at least in part in the object under examination. Further, in the operating state of the system, the ultrasound unit is arranged extracorporeally on the surface of the object under examination.

The medical object (e.g., the optical fiber and the multiple photoacoustic absorbers) and the at least one light source may have all features and properties that were described with respect to the medical object for arrangement in an object under examination and vice versa.

The ultrasound unit may have at least one ultrasound transducer (e.g., multiple ultrasound transducers) that is configured to detect the ultrasound (e.g., the acoustic signal of the ultrasound). Further, the ultrasound unit (e.g., the at least one ultrasound transducer) may be configured to be arranged extracorporeally on a surface (e.g., a skin surface) of the object under examination. The ultrasound unit (e.g., the at least one ultrasound transducer) may be configured to provide the processing unit with a first signal as a function of the received ultrasound.

For example, the ultrasound unit may be configured to detect the ultrasound two-dimensionally (2D) and/or three-dimensionally (3D) on a spatially resolved basis. Further, the ultrasound unit may be configured to detect the ultrasound on a time-resolved basis. The processing unit may be configured to determine (e.g., to reconstruct) the spatial progression of the medical object using the detected ultrasound (e.g., the first signal provided by the ultrasound unit). The processing unit may be configured to determine the spatial progression of the medical object in a coordinate system of the object under examination and/or of the ultrasound unit. For example, the processing unit may be configured to identify a spatial positioning (e.g., position and/or orientation) of the multiple photoacoustic absorbers using the detected ultrasound. Because the multiple photoacoustic absorbers are arranged along the direction of longitudinal extension of the optical fiber and/or along a periphery of the medical object (e.g., in a defined arrangement), the processing unit may be configured to determine the spatial progression of the medical object (e.g., of the optical fiber) using the identified spatial positionings of the multiple photoacoustic absorbers.

The form of embodiment may enable the spatial progression of the part of the medical object arranged in the operating state of the system within the object under examination to be sensed in a precise and patient-friendly manner. For example, using the ultrasound-based sensing of the spatial progression of the medical object, an administration of contrast agent and/or an X-ray dose may be minimized.

In a further form of embodiment of the system, the processing unit may be configured to control the at least one light source for the emission of the excitation light, such that the multiple photoacoustic absorbers are excited sequentially or simultaneously for the photoacoustic emission of the ultrasound. In this case, the excitation light may be configured to excite the multiple photoacoustic absorbers selectively or non-selectively for the photoacoustic emission of the ultrasound.

The at least one light source may be configured to emit the excitation light having at least in part different wavelengths and/or wavelength ranges (e.g., simultaneously, such as superimposed, or sequentially). As a result, the multiple photoacoustic absorbers may be selectively excited by the excitation light at least in part (e.g., completely) for the photoacoustic emission of the ultrasound. Alternatively, the multiple photoacoustic absorbers may be excited non-selectively (e.g., simultaneously) by the excitation light for the photoacoustic emission of the ultrasound. In the event of the excitation (e.g., the non-selective and/or selective excitation) of the multiple photoacoustic absorbers for the emission of the ultrasound, the ultrasound emitted by the individual photoacoustic absorbers may differ at least in part (e.g., completely, such as in the ultrasound intensity and/or the ultrasound wavelength and/or the ultrasound wavelength range). As a result, the detected ultrasound may have a modulation (e.g., a superimposition of ultrasound waves that are emitted by the individual photoacoustic absorbers).

If the optical fiber has multiple core regions that each optically contact one of multiple light sources, the processing unit may be configured to control the multiple light sources (e.g., on a coordinated and/or synchronized basis) for the emission of the excitation light. For example, the processing unit may be configured to control the multiple light sources on a time-sequential and/or modulated basis (e.g., amplitude-modulated and/or chirped) for the emission of the excitation light. As a result, the multiple photoacoustic absorbers may be selectively excited in accordance with the respective optically contacted core region for the photoacoustic emission of the ultrasound.

The processing unit may be configured to identify (e.g., to locate) the multiple photoacoustic absorbers using the detected ultrasound (e.g., individually). Further, as a result, the spatial progression of the medical object may, for example, be determined using the detected ultrasound even in the case of a wound and/or bent and/or twisted arrangement of the medical object in the object under examination.

In a further form of embodiment of the system, the processing unit may be configured to demodulate the detected ultrasound. Further, the processing unit may be configured to identify the multiple photoacoustic absorbers using the demodulated ultrasound.

The demodulation of the detected ultrasound may include a frequency analysis (e.g., a Fourier analysis). In this case, the processing unit may be configured to identify the ultrasound waves emitted in each case by the multiple photoacoustic absorbers (e.g., the respective portion of the detected ultrasound) using the demodulated ultrasound. Further, the processing unit may be configured to identify (e.g., to locate) the multiple photoacoustic absorbers using the demodulated ultrasound (e.g., individually).

As a result, in addition to the spatial progression of the medical object, a spatial positioning (e.g., position and/or orientation) of individual sections of the medical object may be determinable using the detected ultrasound.

In a further form of embodiment of the system, the optical fiber may have the fiber Bragg grating. Further, the system may have a detector. In this case, the optical fiber may optically contact the detector. The detector may further be configured for the detection of a portion of the excitation light reflected off the fiber Bragg grating. Further, the processing unit may be configured to sense a deformation of the optical fiber using the detected excitation light.

The system may further have an optical beam splitter that is configured to create an optical contact between the optical fiber (e.g., the core region of the optical fiber), the at least one light source, and the detector. For this, the optical beam splitter may have three optical contact surfaces. The optical fiber, the at least one light source, and the detector may optically contact the beam splitter on in each case one of the three optical contact surfaces of the beam splitter. As a result, the detector and the at least one light source may optically contact the optical fiber at a common end of the optical fiber (e.g., a common optical contact surface). If the optical fiber has multiple core regions with in each case a fiber Bragg grating, the system may in each case have an optical beam splitter and in each case a detector for each of the core regions.

The detector may be configured to detect the portion of the excitation light reflected off the fiber Bragg grating. The detector may further be configured to provide the processing unit with a second signal as a function of the detected portion of the excitation light (e.g., as a function of a wavelength and/or of a wavelength range of the detected portion of the excitation light). The processing unit may further be configured to sense the deformation (e.g., expansion and/or compression) of the optical fiber using the second signal (e.g., using the detected portion of the excitation light) (this is known as shape sensing). The processing unit may be configured to determine the spatial progression of the medical object additionally using the sensed deformation of the optical fiber (e.g., as a boundary condition).

Because the optical fiber has the multiple photoacoustic absorbers and the fiber Bragg grating, the detected ultrasound may be registered with the second signal (e.g., the sensed deformation of the optical fiber). As a result, the spatial progression of the medical object may be determined particularly precisely (e.g., additionally using the second signal). If the optical fiber has multiple core regions with in each case a fiber Bragg grating, the processing unit may be configured to sense a three-dimensional spatial progression of the optical fiber using the second signal of the multiple detectors.

In a further form of embodiment of the system, the ultrasound unit may have multiple ultrasound transducers that are arranged in a line array and/or a matrix array.

The ultrasound unit may have multiple ultrasound transducers that may be arranged in a spatial arrangement as a 1D array or a 2D array (e.g., in the shape of a grating and/or concentrically). Further, the multiple ultrasound transducers may be arranged along a curved surface in the line array and/or matrix array. The ultrasound unit may be configured for the 2D and/or 3D spatially resolved detection of the ultrasound. As a result, a precise determination of the spatial progression of the medical object is enabled using the detected ultrasound.

In a further form of embodiment of the system, the processing unit may be configured to receive a dataset having a mapping and/or a model of the object under examination. Further, the processing unit may be configured to provide a superimposition dataset using the dataset and the detected ultrasound.

The receipt of the dataset may, for example, include the sensing and/or reading of a computer-readable data store and/or the receipt from a data storage unit (e.g., a database). Further, the dataset may be provided by a medical imaging device (e.g., the ultrasound unit).

The dataset may have a 2D and/or 3D mapping (e.g., a time-resolved 2D and/or 3D mapping) of the object under examination (e.g., of the hollow organ). For example, the dataset may have a contrasted and/or segmented mapping of the object under examination (e.g., of the hollow organ). Further, the dataset may map the object under examination preoperatively and/or intraoperatively. Alternatively or additionally, the dataset may have a 2D and/or 3D model (e.g., a central line model and/or a volume model, such as a volume mesh model) of the object under examination (e.g., of the hollow organ).

To record the dataset, the ultrasound unit (e.g., the at least one ultrasound transducer) may be configured to emit an ultrasound field. Further, the ultrasound unit (e.g., the at least one ultrasound transducer) may be configured to detect a reflected portion of the ultrasound field (e.g., resolved in 2D and/or 3D space). Further, the ultrasound unit (e.g., the at least one ultrasound transducer) may be configured to detect the reflected portion of the ultrasound field on a time-resolved basis. The ultrasound unit may be further configured to provide the processing unit with the first signal additionally as a function of the detected ultrasound field. The processing unit may further be configured to generate (e.g., to reconstruct) the dataset using the detected ultrasound field (e.g., the first signal). The dataset may, as a result, be inherently registered with the detected ultrasound.

Alternatively, the medical imaging device for recording and/or providing the dataset may be different from the ultrasound unit. For example, the medical imaging device may be configured as a magnetic resonance system (MRT) and/or a computed tomography system (CT) and/or a medical X-ray device and/or a positron emission tomography system (PET) and/or an ultrasound device.

The processing unit may be configured to register the dataset with the coordinate system of the object under examination and/or of the ultrasound unit. As a result, the dataset may be registered with the detected ultrasound. Providing the optical fiber has a fiber Bragg grating, the processing unit may be further configured to register the second signal and/or the third signal with the dataset.

The processing unit may also be configured to provide the superimposition dataset using the dataset and the detected ultrasound. In this case, the provision of the superimposition dataset may include a superimposition and/or averaging and/or merging (e.g., an at least partial and/or region-by-region and/or adaptive superimposition and/or averaging and/or merging) of the dataset and of the detected ultrasound. The superimposition dataset may have the mapping and/or the model of the object under examination (e.g., of the hollow organ) and a mapping and/or a model of the medical object (e.g., the multiple photoacoustic absorbers). The model of the medical object (e.g., of the multiple photoacoustic absorbers) may, for example, include a virtual (e.g., abstracted) representation of the medical object and/or of the multiple photoacoustic absorbers. The processing unit may be configured to superimpose and/or average the mapping and/or the model of the medical object (e.g., of the multiple photoacoustic absorbers) in accordance with the spatial progression of the medical object with respect to the dataset.

The provision of the superimposition dataset may further include storage on a computer-readable storage medium and/or a display of a graphical visualization of the superimposition dataset on a visualization unit. In this case, the processing unit may be configured for the repeated and/or continuous provision of the superimposition dataset. As a result, a user (e.g., a member of medical operating personnel) may be supported during monitoring and/or navigation of the medical object.

In a further form of embodiment of the system, the processing unit may be configured to determine a spatial positioning of one of the multiple photoacoustic absorbers using the detected ultrasound. Further, the processing unit may be configured to control the multiple ultrasound transducers based on the spatial positioning of the photoacoustic absorber, such that an ultrasound field is emitted in two orthogonal planes. In the operating state of the system, an axis of intersection of both the orthogonal planes may in this case run through the photoacoustic absorber. Further, the multiple ultrasound transducers may be configured to detect a reflected portion of the ultrasound field. Further, the processing unit may be configured to generate the dataset having an intraoperative mapping of the object under examination using the detected ultrasound field.

The ultrasound unit may have multiple ultrasound transducers that are arranged in a line array and/or a matrix array. As a result, a 2D and/or 3D spatially resolved detection of the ultrasound emitted by the photoacoustic absorber may be enabled by the ultrasound unit (e.g., the multiple ultrasound transducers). For example, the processing unit may be configured to determine the spatial positioning of one (e.g., a selected one) of the multiple photoacoustic absorbers using the detected ultrasound. The processing unit may be configured to select the photoacoustic absorber that, in the operating state of the system, is arranged within a sensing region of the ultrasound unit. Providing that, in the operating state, multiple photoacoustic absorbers are arranged in the sensing region of the ultrasound unit, the processing unit may be configured to select the photoacoustic absorber that is arranged along the direction of longitudinal extension of the medical object distally with respect to the remaining photoacoustic absorbers. Alternatively, the photoacoustic absorber may be selected and/or predefined by a user (e.g., using a user input using an input unit). The processing unit may be configured to determine the spatial positioning of the photoacoustic absorber (e.g., selected photoacoustic absorber) in the coordinate system of the object under examination and/or the ultrasound unit.

The multiple ultrasound transducers may be configured for the emission of an ultrasound field. The multiple ultrasound transducers each have at least one first generation unit (e.g., a piezoelectric crystal and/or a photoacoustic generation unit) that is configured to generate the ultrasound field (e.g., sound waves) as a function of a control signal from the processing unit (e.g., in a gated and/or pulsed and/or continuous manner) by pressure variations. In this case, the ultrasound field may describe a field of a spatial propagation of the sound waves. The processing unit may be configured to control the ultrasound unit such that a beam orientation and/or beamforming of the ultrasound field may be adjusted.

In this case, the processing unit may be configured to control the multiple ultrasound transducers, based on the spatial positioning (e.g., the current spatial positioning) of the photoacoustic absorber (e.g., selected photoacoustic absorber) such that the ultrasound field is emitted in two planes orthogonal to one another. The axis of intersection of both the orthogonal planes runs through the photoacoustic absorber in the operating state of the system.

The multiple ultrasound transducers may be further configured to detect the reflected portion of the ultrasound field (e.g., resolved in 2D and/or 3D space). Further, the multiple ultrasound transducers may be configured to detect the reflected portion of the ultrasound field on a time-resolved basis. The ultrasound unit may further be configured to provide the processing unit with the first signal additionally as a function of the detected ultrasound field.

The processing unit may further be configured to generate (e.g., to reconstruct) the dataset having the intraoperative mapping of the object under examination using the detected ultrasound field (e.g., the first signal). The intraoperative mapping of the object under examination may in this case have two 2D spatially resolved partial mappings of the object under examination along the two orthogonal planes of the ultrasound field. The photoacoustic absorber (e.g., the selected photoacoustic absorber) is mapped in both partial mappings.

As a result, the photoacoustic absorber is always mapped in the dataset (e.g., the intraoperative mapping of the object under examination). Further, the spatial positioning of the photoacoustic absorber may be determined by the mapping in both the orthogonal planes three-dimensionally with respect to the coordinate system of the ultrasound unit and/or with respect to the coordinate system of the object under examination.

In a further form of embodiment of the system, the system may further have a medical imaging device that is configured to record and/or provide the dataset.

In this case, the medical imaging device may, for example, be configured as a magnetic resonance system and/or a computed tomography system and/or a medical X-ray device and/or a positron emission tomography system and/or an ultrasound device.

The medical imaging device may be configured for the preoperative and/or intraoperative recording of the dataset. Further, the medical imaging device may be configured for the repeated recording and/or for the repeated provision of the dataset. In this case, the dataset may include medical image data recorded by the medical imaging device. In this case, the medical image data may have a mapping (e.g., a preoperative and/or intraoperative mapping) of the object under examination.

The spatial progression of the medical object may be determined with respect to the dataset and/or provided by the superimposition dataset.

In a further form of embodiment of the system, the processing unit may be configured to identify anatomical and/or geometric features of the object under examination and/or of a further medical object arranged therein in the dataset. Further, the processing unit may be configured to determine the spatial progression of the medical object with respect to the identified anatomical and/or geometric features.

The dataset may, for example, have all features and properties that are described with respect to other advantageous forms of embodiment of the system and vice versa.

The geometric features may, for example, include lines (e.g., contours and/or edges) and/or corners and/or contrast transitions and/or a spatial arrangement of the aforementioned features. The anatomical features may, for example, include anatomical landmarks and/or tissue borders (e.g., a wall of a vessel and/or organ) and/or special anatomical features (e.g., a bifurcation and/or an ostium). The dataset may have multiple image points (e.g., pixels and/or voxels), each with an image value (e.g., an intensity value) and/or an image value progression (e.g., a time intensity curve), that correspond in each case to a spatial position in the object under examination. In this case, the processing unit may be configured to identify the geometric and/or anatomical features using the image values of the image points of the dataset. Further, the processing unit may be configured to identify the geometric and/or anatomical features using a classification of static and/or moving regions in the dataset (e.g., using the image value progressions, such as the time intensity curves). Further, the apparatus may be configured to identify the geometric and/or anatomical features in the dataset thanks to a comparison with a threshold value and/or with an anatomy atlas and/or thanks to the use of a trained function and/or of an algorithm for pattern recognition.

The further medical object may, for example, be configured as a diagnostic and/or medical instrument (e.g., as a catheter and/or endoscope and/or guide wire). Further, the further medical object may be configured as an implant (e.g., as a stent, such as a fenestrated stent). The processing unit may be configured to identify (e.g., to locate) the further medical object using the identified anatomical and/or geometric features in the dataset. For this, the further medical object may have at least one marker structure that is mapped in the dataset.

Further, the processing unit may be configured to determine the spatial progression of the medical object with respect to the identified anatomical and/or geometric features. For example, the processing unit may be configured to determine a measurement of distance and/or a direction vector between at least one section of the medical object (e.g., at least one of the multiple photoacoustic absorbers) and at least one of the identified anatomical and/or geometric features. Further, the visualization unit may be configured to display the measurement of distance and/or the direction vector and/or a workflow reference in addition to the superimposition dataset. As a result, an improved navigation of the medical object may be enabled.

In a further form of embodiment of the system, the system may further have a movement apparatus for the robotic movement of the ultrasound unit. In this case, the movement apparatus may be configured to position the ultrasound unit. Further, the processing unit may be configured to control the movement apparatus based on the detected ultrasound.

The movement apparatus may be configured to stop and/or move the ultrasound unit. For example, the movement apparatus may be configured to position the first ultrasound unit. In this case, the positioning of the ultrasound unit by the movement apparatus may, for example, include a translation and/or rotation and/or tilting of the ultrasound unit and/or the individual components thereof (e.g., of the at least one ultrasound transducer). The movement apparatus may, for example, include a robot arm that is coupled in movement (e.g., pneumatically and/or electromagnetically and/or mechanically) to the ultrasound unit (e.g., the at least one ultrasound transducer). The processing unit may be configured to adjust the positioning of the ultrasound unit thanks to a controller of the movement apparatus. For this, the processing unit may be communicatively coupled to the movement apparatus. In this case, the processing unit may be configured to control the movement apparatus based on the detected ultrasound (e.g., the spatial progression of the medical object). For example, the movement apparatus may be configured to arrange the ultrasound unit in the operating state of the system on the surface of the object under examination and to position the ultrasound unit (e.g., orient the ultrasound unit), such that the multiple photoacoustic absorbers are arranged at least in part in the sensing region of the ultrasound unit. Further, the movement apparatus may be configured to adjust the positioning of the ultrasound unit (e.g., repeatedly).

As a result, a particularly flexible and/or customized detection of the ultrasound by the ultrasound unit (e.g., the at least one ultrasound transducer) may be enabled.

BRIEF DESCRIPTION OF THE DRAWINGS

Exemplary embodiments are represented in the drawings and are described in greater detail below. The same reference characters are used for the same features in different figures, in which.

DETAILED DESCRIPTION

Figure 1:
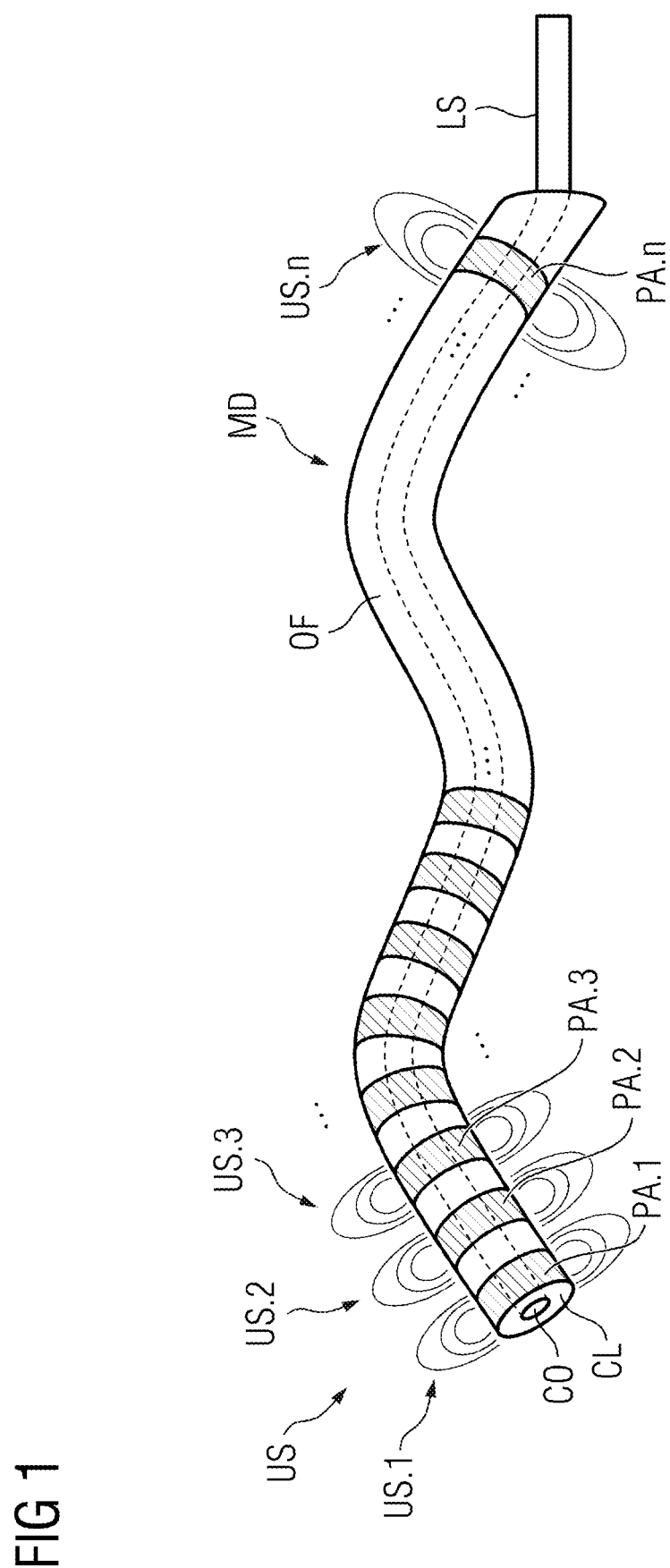
FIGS. 1 and 2 show schematic representations of different forms of embodiment of a medical object.

FIG. 1 shows a schematic representation of an embodiment of a medical object MD. In this case, the medical object MD may have an optical fiber OF that is configured to contact at least one light source LS optically. The medical object MD may have multiple photoacoustic absorbers PA.1, PA.2, PA.3 to PA.n that are arranged in sections along a direction of longitudinal extension of the optical fiber OF. The multiple photoacoustic absorbers PA.1 to PA.n may be configured to be arranged at least in part in an object under examination. Further, the optical fiber OF may be configured to conduct an excitation light emitted by the at least one light source LS to the multiple photoacoustic absorbers PA.1 to PA.n. In this case, the optical fiber OF may, at least in sections, have a sheathing CL that is configured to prevent an escape of the excitation light as a result of its being reflected off a boundary surface between a core region CO of the optical fiber OF and the sheathing CL. Further, the multiple photoacoustic absorbers PA.1 to PA.n may be configured to be excited by the excitation light for the photoacoustic emission of ultrasound US. In this case, the ultrasound US emitted by the multiple photoacoustic absorbers PA.1 to PA.n is, for example, schematically represented in FIG. 1 as a superimposition of the individual ultrasound waves US.1 to US.n.

Figure 2:
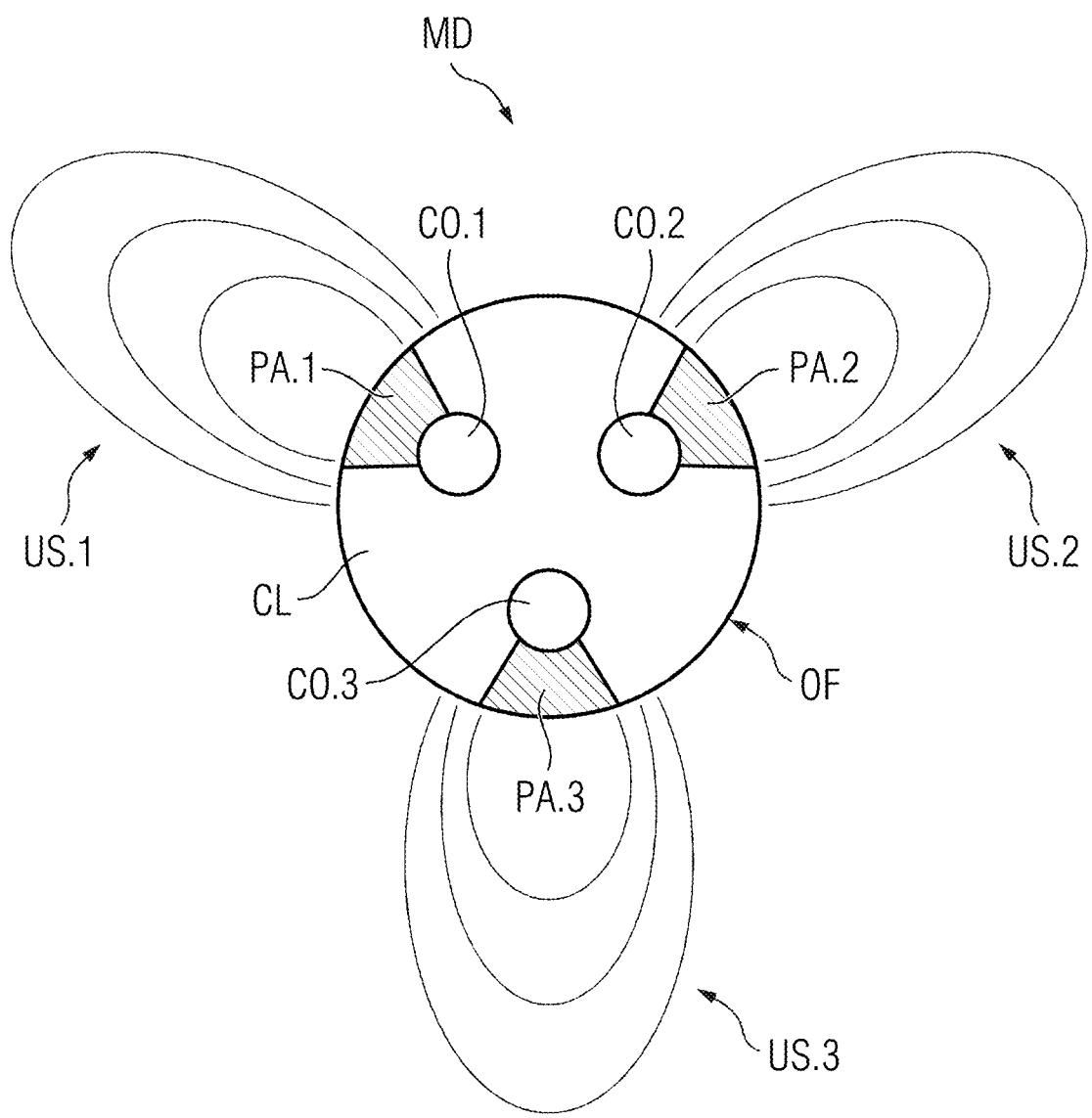

FIG. 2 shows a schematic representation of a further form of embodiment of a medical object MD. In this case, a cross-section of the medical object MD with respect to a direction of longitudinal extension of the medical object MD is schematically represented in FIG. 2. The optical fiber OF may have multiple (e.g., three) core regions CO.1, CO.2 and CO.3 that run along the direction of longitudinal extension of the optical fiber OF. In this case, the multiple core regions CO.1, CO.2 and CO.3 may be configured to contact a light source LS optically in each case. Further, the medical object MD may have a sector along a periphery of the medical object MD that, in each case, is radial to the multiple core regions CO.1, CO.2 and CO.3. In this case, the multiple photoacoustic absorbers PA.1, PA.2, and PA.3 may in each case be arranged in one of the radial sectors of the medical object MD and in each case may optically contact one of the core regions CO.1, CO.2, and CO.3. The core regions CO.1, CO.2, and CO.3 may further be configured to conduct the excitation light emitted by the, in each case, optically contacted light source LS to the multiple photoacoustic absorbers PA.1, PA.2 and PA.3.

Figure 3:
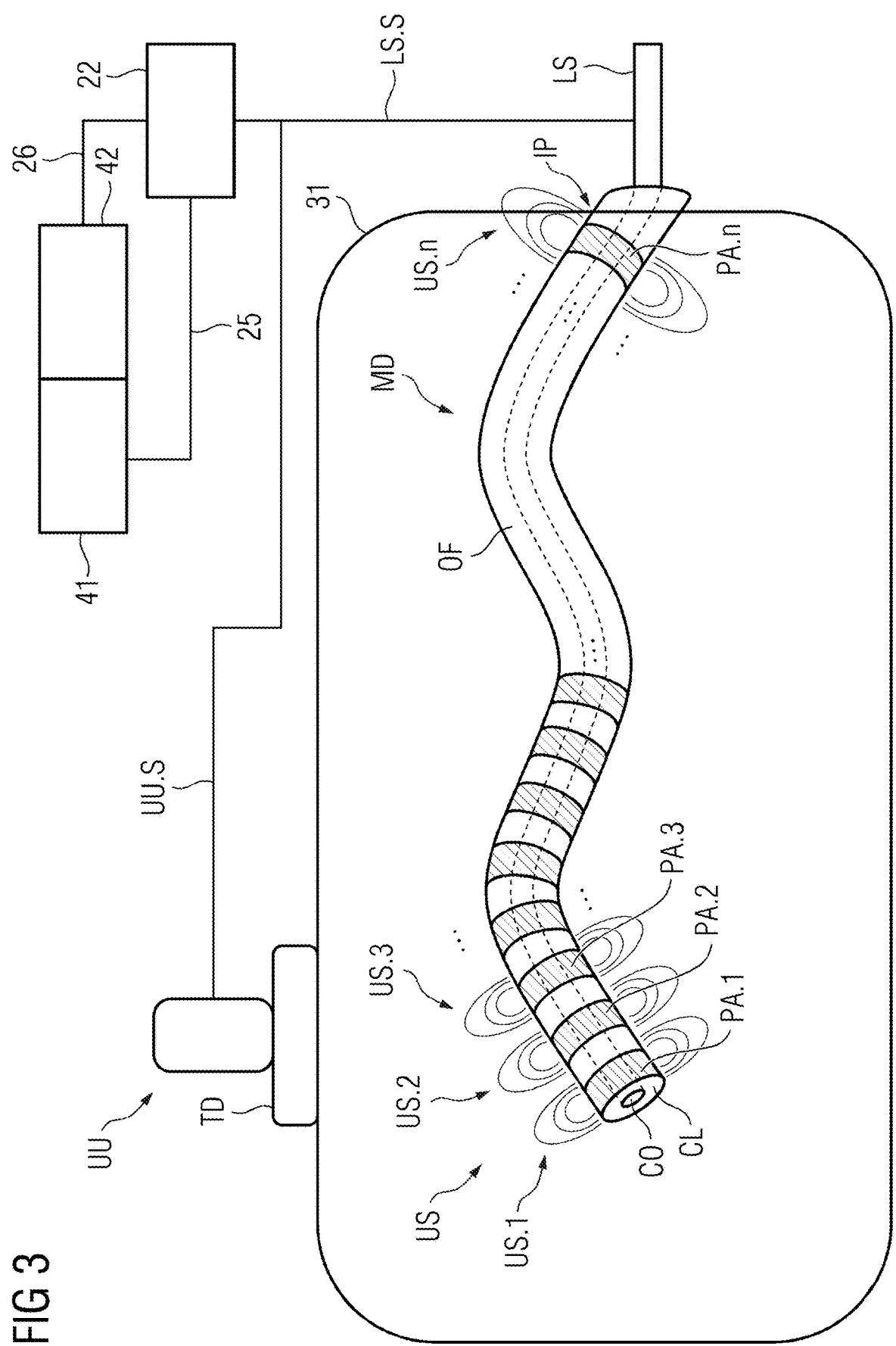
FIG. 3 shows a schematic representation of a form of embodiment of a proposed system.

FIG. 3 shows a schematic representation of a form of embodiment of a system for sensing a medical object MD. In this case, the system may have the medical object MD, a processing unit 22, at least one light source LS, and an ultrasound unit UU. The at least one light source LS may be configured to emit the excitation light (e.g., to feed the excitation light into the optical fiber OF). If the optical fiber OF has multiple core regions CO.1 to CO.3, the system may have multiple light sources. The multiple core regions CO.1 to CO.3 each optically contact one of the light sources (not shown here). In this case, the excitation light may be configured to excite the multiple photoacoustic absorbers PA.1 to PA.n for the photoacoustic emission of the ultrasound US.

The ultrasound unit UU may have at least one ultrasound transducer TD (e.g., multiple ultrasound transducers TD) that is configured to detect the ultrasound US (e.g., the acoustic signal of the ultrasound US). In this case, the ultrasound unit UU (e.g., the at least one ultrasound transducer TD) may be configured to be arranged extracorporeally on a surface (e.g., a skin surface) of the object under examination 31. The ultrasound unit UU (e.g., the at least one ultrasound transducer TD) may be configured to provide the processing unit 22 with a first signal UU.S as a function of the received ultrasound.

The processing unit 22 may be configured to determine a spatial progression of the medical object MD using the detected ultrasound US (e.g., using the first signal UU.S). The optical fiber OF may optically contact the at least one light source LS in an operating state of the system. Further, the multiple photoacoustic absorbers PA.1 to PA.n (e.g., the medical object MD) may be arranged in the operating state of the system at least in part in the object under examination 31. Further, in the operating state of the system, the ultrasound unit UU (e.g., the at least one ultrasound transducer TD) may be arranged extracorporeally on the surface of the object under examination 31.

The ultrasound unit UU may have multiple ultrasound transducers TD that are arranged in a line array and/or a matrix array.

Further, the multiple photoacoustic absorbers PA.1 to PA.n may at least in part (e.g., completely) have different excitation sensitivities for the photoacoustic emission of the ultrasound US. In this case, the excitation light may be configured to excite the multiple photoacoustic absorbers PA.1 to PA.n selectively or non-selectively for the photoacoustic emission of the ultrasound US. Further, the processing unit 22 may be configured to control the at least one light source LS for the emission of the excitation light (e.g., using the signal LS.S), such that the multiple photoacoustic absorbers PA.1 to PA.n are excited sequentially or simultaneously for the photoacoustic emission of the ultrasound US.

The processing unit 22 may further be configured to demodulate the detected ultrasound US and to identify the multiple photoacoustic absorbers PA.1 to PA.n using the demodulated ultrasound.

The system may further include an input unit 42 (e.g., a keyboard) and/or a visualization unit 41 (e.g., a monitor and/or display). The input unit 42 may be integrated into the visualization unit 41 (e.g., in the case of a capacitive and/or resistive input display).

The visualization unit 41 may be configured to display information and/or graphical representations of information of the system and/or of the processing unit 22 and/or of further components (e.g., a graphical representation of the detected ultrasound). For this, the processing unit 22 may, for example, send a signal 25 to the visualization unit 41. The input unit 42 may be configured for sensing a user input and for providing a signal 26 as a function of the user input.

Figure 4:
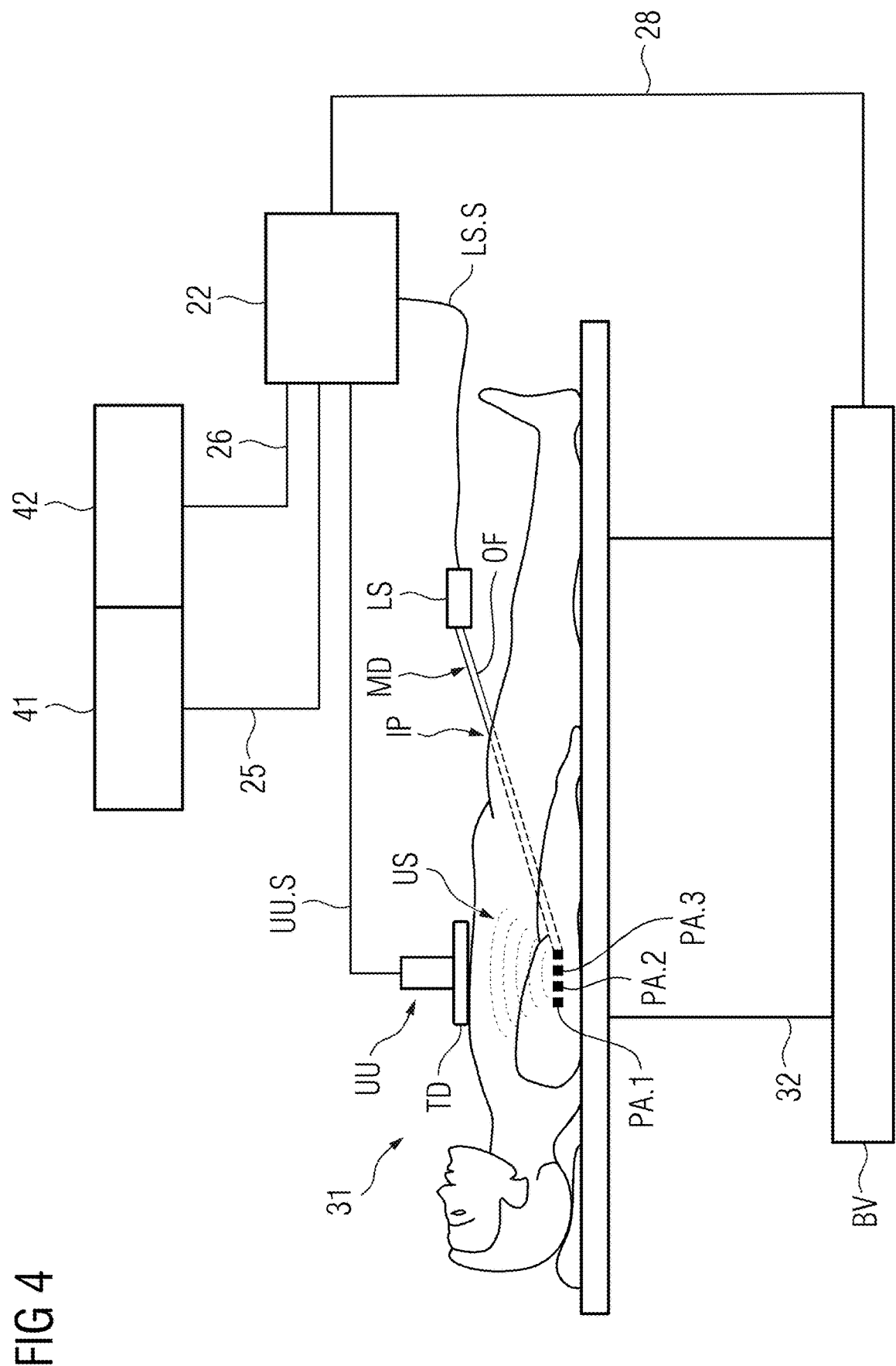
FIG. 4 shows a schematic representation of an exemplary arrangement of the system.

FIG. 4 schematically represents an exemplary arrangement of a form of embodiment of the system. In this case, the medical object MD and the multiple photoacoustic absorbers PA.1 to PA.n may, in the operating state of the system, be arranged at least in part in the object under examination 31 (e.g., in a hollow organ of the object under examination 31). The object under examination 31 may be arranged on a patient positioning apparatus 32. The patient positioning apparatus 32 may be movable, at least in part. For this, the patient positioning apparatus 32 may have a movement unit BV that may be controlled by the processing unit 22 using a signal 28.

Figure 5:
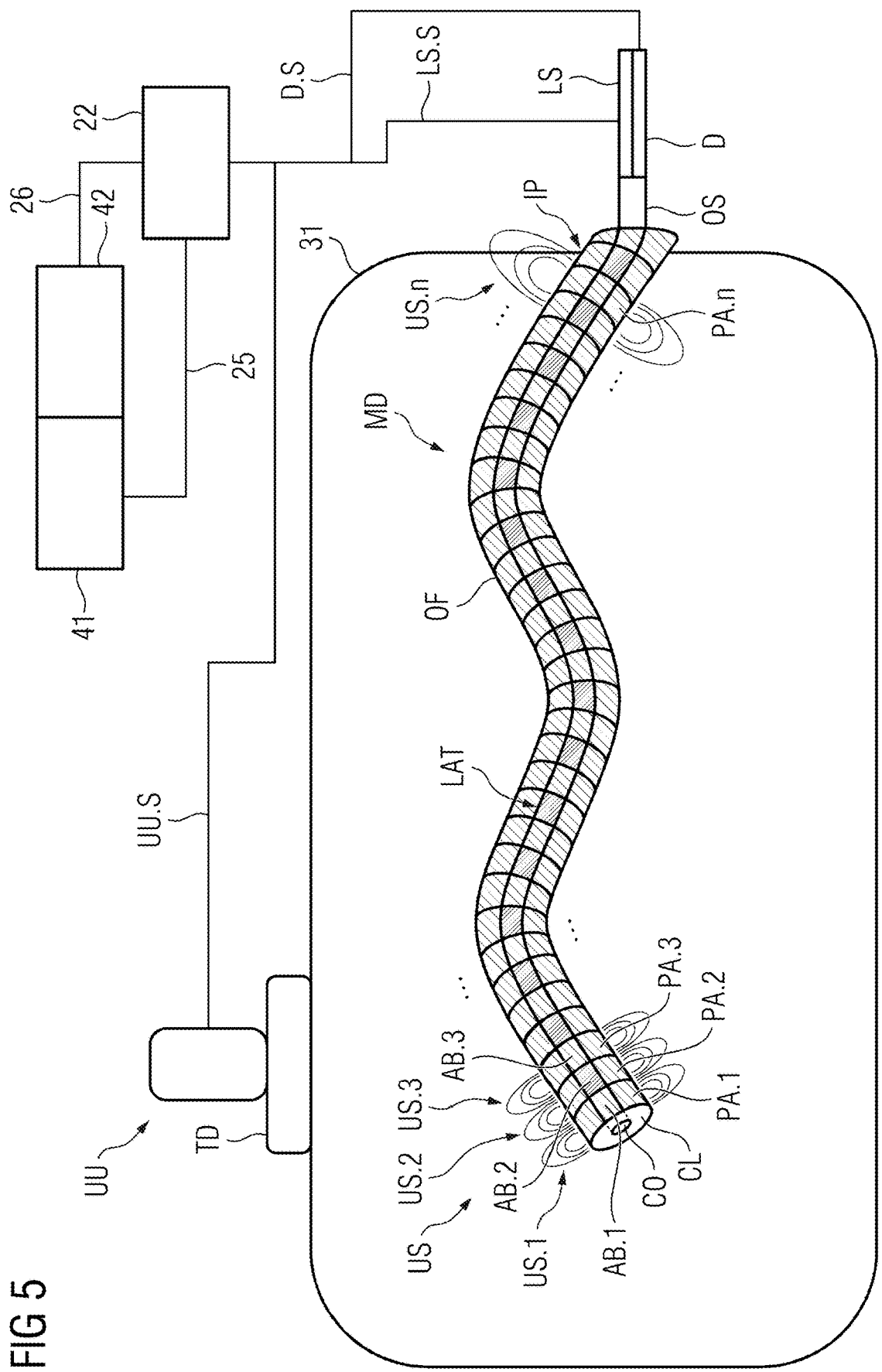
FIGS. 5 to 8 show schematic representations of different forms of embodiment of a system.

FIG. 5 shows a schematic representation of a further form of embodiment of the system. In this case, the optical fiber OF (e.g., the core region CO) may have a fiber Bragg grating LAT that has a periodic arrangement of sections AB.1, AB.2, AB.3 to AB.n along the direction of longitudinal extension of the optical fiber OF. In this case, adjacent sections may in each case have different refractive indices. The multiple photoacoustic absorbers PA.1 to PA.n may each be arranged on one of the sections of the fiber Bragg grating LAT. In this case, the fiber Bragg grating may be configured to filter the excitation light in the sections AB.1 to AB.n (e.g., differently). Further, the filtered excitation light may be configured to excite the multiple photoacoustic absorbers PA.1 to PA.n for the modulated emission of the ultrasound US.

The system may further include a detector D. The optical fiber OF optically contacts the detector D. For this, the system may have an optical beam splitter OS that is configured to produce an optical contact between the optical fiber OF, the at least one light source LS, and the detector D. In this case, the detector D may be configured to detect a portion of the excitation light reflected off the fiber Bragg grating LAT and to provide the processing unit 22 with a corresponding signal D.S. Further, the processing unit 22 may be configured to sense a deformation of the optical fiber OF using the detected excitation light (e.g., using the signal D.S.).

Figure 6:
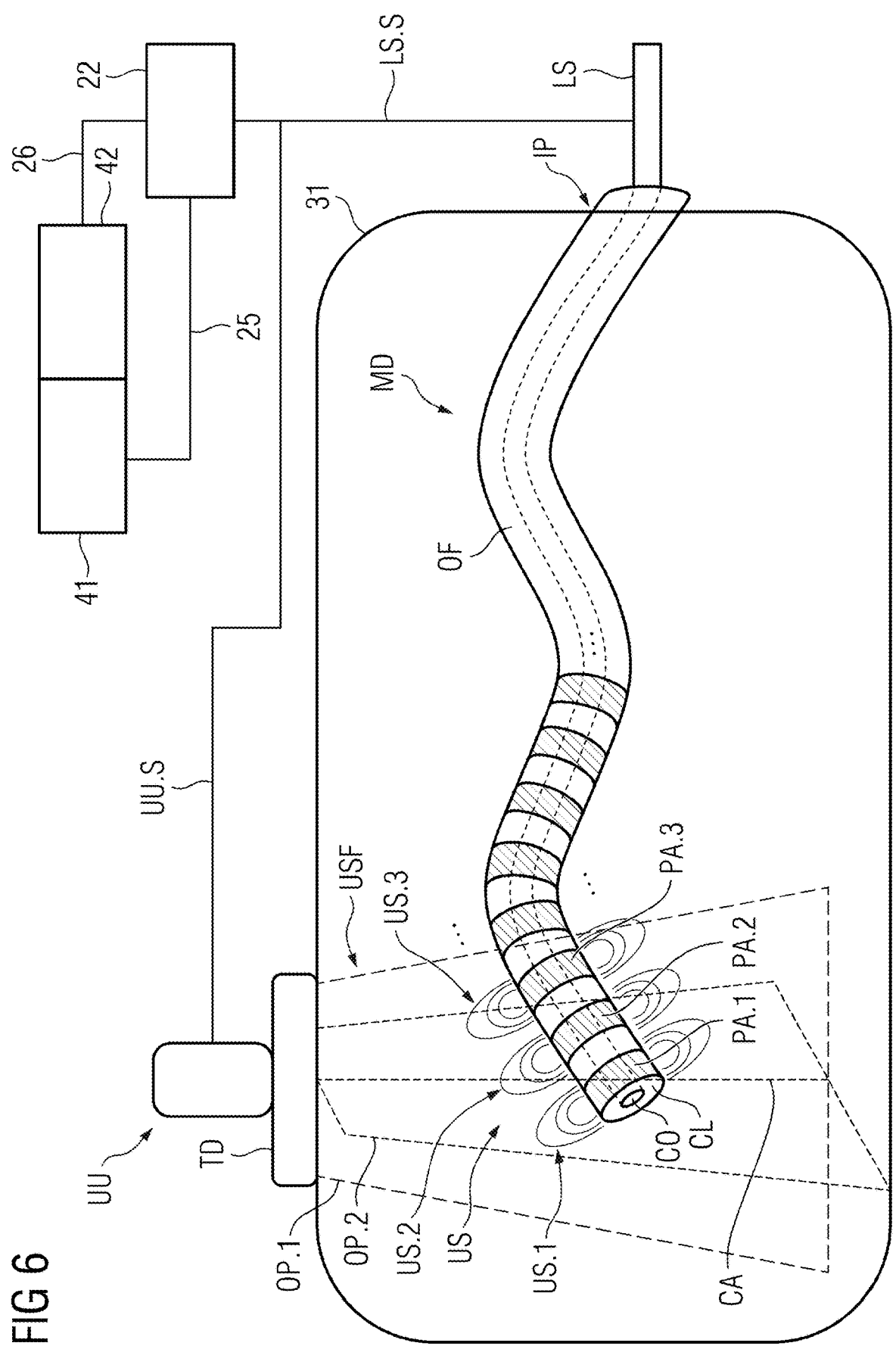

FIG. 6 schematically represents a further form of embodiment of the system. In this case, the ultrasound unit UU may have multiple ultrasound transducers TD that are arranged in a line array and/or a matrix array. Further, the processing unit 22 may be configured to determine a spatial positioning of one of the multiple photoacoustic absorbers PA.1 to PA.n (e.g., the photoacoustic absorber PA.1) using the detected ultrasound US. Further, the processing unit 22 may be configured to control the multiple ultrasound transducers TD based on the spatial positioning of the photoacoustic absorber PA.1, such that an ultrasound field USF is emitted in two orthogonal planes OP.1 and OP.2. Further, in the operating state of the system, an axis of intersection CA of both the orthogonal planes OP.1 and OP.2 may run through the photoacoustic absorber PA.1. Further, the multiple ultrasound transducers TD may be further configured to detect a reflected portion of the ultrasound field USF. The ultrasound unit UU may further be configured to provide the processing unit 22 with the first signal UU.S additionally as a function of the detected ultrasound field USF. In this case, the processing unit 22 may further be configured to generate a dataset having an intraoperative mapping of the object under examination 31 using the detected ultrasound field USF (e.g., the first signal UU.S). Further, the processing unit 22 may be configured to provide a superimposition dataset using the dataset and the detected ultrasound US. The visualization unit 41 may be configured to display a graphical representation of the superimposition dataset.

Figure 7:
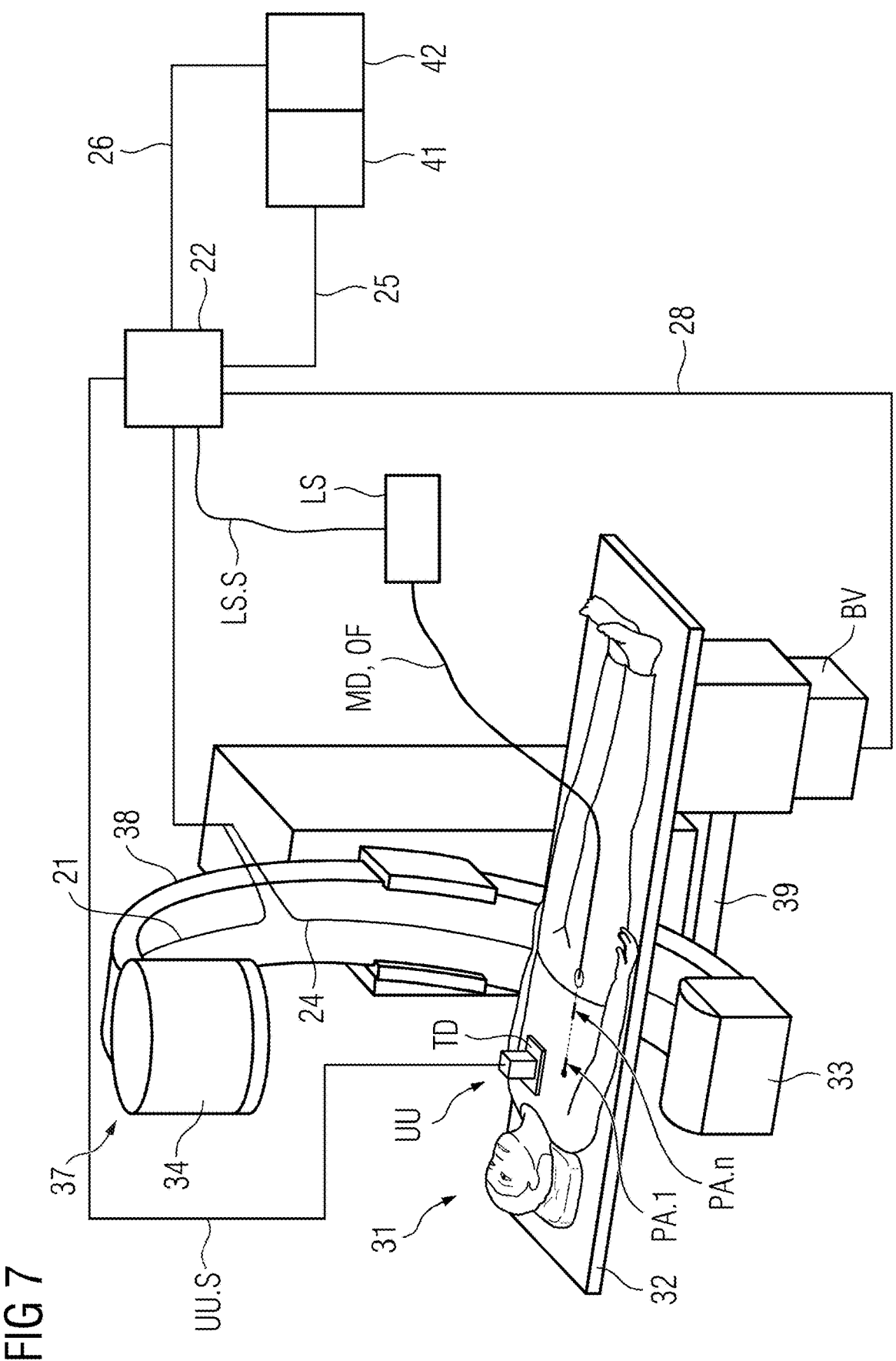

FIG. 7 shows a schematic representation of a further form of embodiment of the system. In this case, the system may further have a medical imaging device (e.g., a medical C-arm X-ray device 37) that is configured to record and/or provide the dataset. The medical C-arm X-ray device 37 may have a detector 34 (e.g., an X-ray detector) and an X-ray source 33. For the recording of the dataset (e.g., the preoperative and/or intraoperative recording of the dataset), the arm 38 of the medical C-arm X-ray device 37 may be movably mounted about one or more axes. Further, the medical C-arm-X ray device 37 may include a further movement unit 39 (e.g., a system of wheels and/or a system of rails and/or a robot arm) that enables the medical C-arm X-ray device 37 to move in space. The detector 34 and the X-ray source 34 may be movably fastened to a common C-arm 38 in a defined arrangement.

The processing unit 22 may be configured to control a positioning of the medical C-arm X-ray device 37 relative to the object under examination 31. The positioning of the medical C-arm X-ray device 37 relative to the object under examination 31 may, for example, include a positioning of the defined arrangement of X-ray source 33 and detector 34 (e.g., of the C-arm 38) about one or more spatial axes.

To record the dataset of the object under examination 31, the processing unit 22 may send a signal 24 to the X-ray source 33. The X-ray source 33 may then emit an X-ray beam (e.g., a cone beam and/or fan beam and/or parallel beam). When the X-ray beam, after an interaction with a region of the object under examination 31 to be mapped, hits a surface of the detector 34, the detector 34 may send a signal 21 to the processing unit 22. The processing unit 22 may, for example, receive the dataset using the signal 21. Further, the visualization unit 41 may be configured to display a graphical representation of the dataset (e.g., using the signal 25).

The processing unit 22 may be configured to identify anatomical and/or geometric features of the object under examination 31 and/or of a further medical object arranged therein in the dataset. Further, the processing unit 22 may be configured to determine the spatial progression of the medical object MD with respect to the identified anatomical and/or geometric features.

Figure 8:
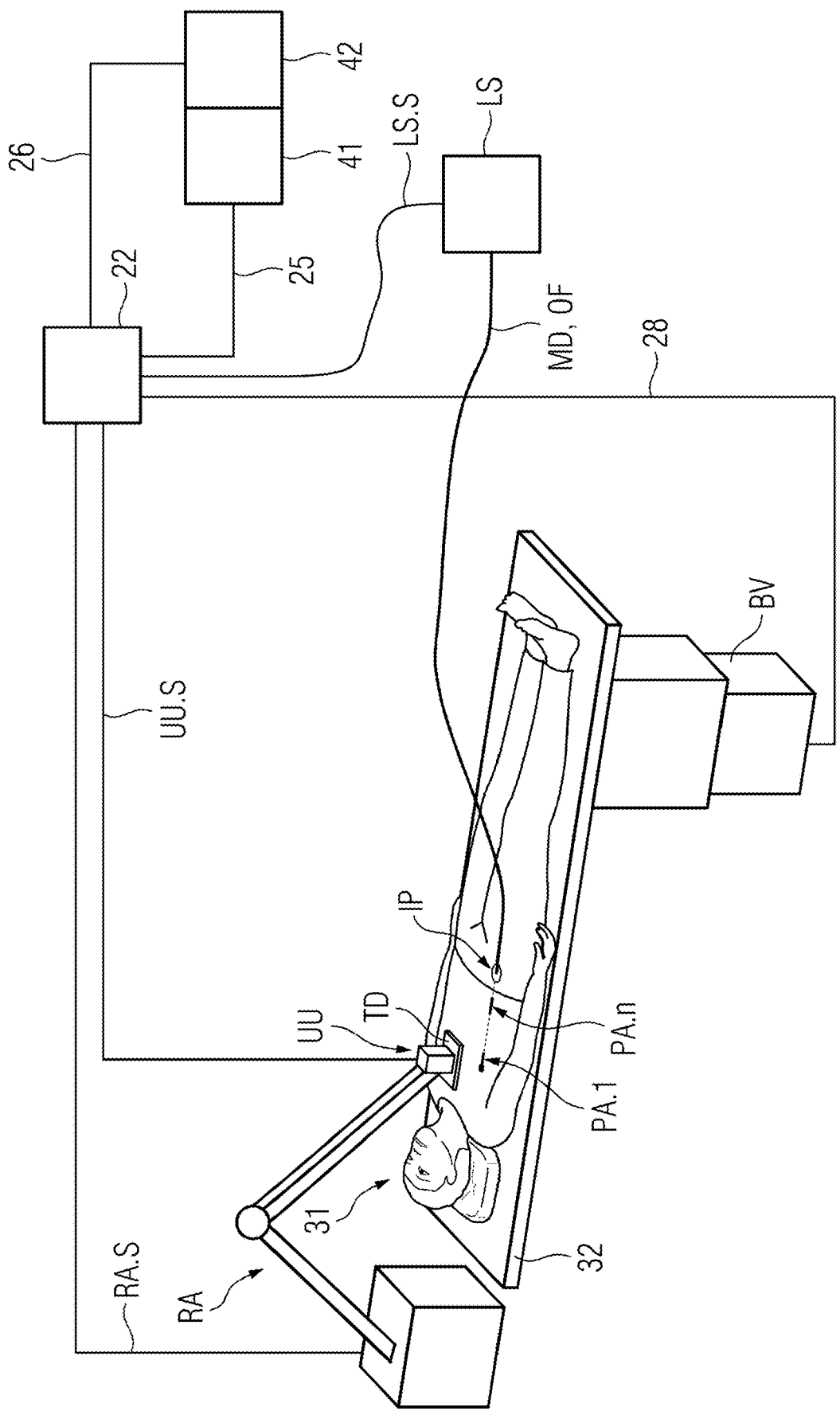

FIG. 8 shows a schematic representation of a further form of embodiment of the system. In this case, the system may further have a movement apparatus RA.

The movement apparatus RA may be configured for the robotic movement of the ultrasound unit UU. The movement apparatus RA may be configured to stop and/or move the ultrasound unit UU. For example, the movement apparatus RA may be configured to position the ultrasound unit UU (e.g., the at least one ultrasound transducer TD). In this case, the positioning of the ultrasound unit UU by the movement apparatus RA may, for example, include a translation and/or rotation of the ultrasound unit UU.1 and/or the individual components thereof (e.g., of the at least one ultrasound transducer TD). The movement apparatus RA may, for example, include a robot arm that is coupled in movement (e.g., pneumatically and/or electromagnetically and/or mechanically) to the ultrasound unit UU (e.g., the at least one ultrasound transducer TD). For example, the movement apparatus RA may be configured to arrange the ultrasound unit UU in the operating state of the system on the surface of the object under examination 31 and to position the ultrasound unit UU (e.g., orient the ultrasound unit UU), such that the multiple photoacoustic absorbers PA.1 to PA.n are arranged at least in part in a sensing region of the ultrasound unit UU (e.g., of the at least one ultrasound transducer TD). Further, the processing unit 22 may be configured to control the movement apparatus RA based on the detected ultrasound US (e.g., using a signal RA.S.).

The schematic representations contained in the figures described in no way map the scale or size ratio.

The apparatuses and methods described in detail above are merely exemplary embodiments that may be modified in a wide variety of ways by the person skilled in the art, without departing from the scope of the invention. Further, the use of the indefinite article "a" or "an" does not rule out that the features in question may also be present multiple times. Likewise, the terms "unit" and "element" do not rule out that the components in question consist of multiple interacting subcomponents that, where appropriate, may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical object for arrangement in an object under examination, the medical object comprising:
    an optical fiber configured to contact at least one light source optically;
    multiple photoacoustic absorbers that are arranged in sections along a direction of longitudinal extension of the optical fiber, along a periphery of the optical fiber, or along the direction of longitudinal extension of the optical fiber and along the periphery of the optical fiber,
    wherein the optical fiber comprises a sheathing, a portion of the sheathing being arranged between adjacent photoacoustic absorbers of the multiple photoacoustic absorbers,
    wherein the multiple photoacoustic absorbers are configured to be arranged at least in part in the object under examination,
    wherein the optical fiber is configured to conduct an excitation light emitted by the at least one light source to the multiple photoacoustic absorbers, and
    wherein the multiple photoacoustic absorbers are configured to be excited by the excitation light for photoacoustic emission of ultrasound.

2. The medical object of claim 1, wherein the multiple photoacoustic absorbers have at least in part different excitation sensitivities for the photoacoustic emission of the ultrasound.

3. The medical object of claim 1, wherein the optical fiber has multiple core regions that run along the direction of longitudinal extension of the optical fiber,
    wherein the multiple core regions are configured in each case to contact a light source optically,
    wherein the medical object has a sector along a periphery of the medical object that in each case is radial to the multiple core regions, wherein the multiple photoacoustic absorbers are in each case arranged in one of the radial sectors of the medical object and in each case contact one of the multiple core regions optically, and wherein the multiple core regions are configured to conduct the excitation light emitted by the in each case optically contacted light source to the multiple photoacoustic absorbers.

4. The medical object of claim 1, wherein the optical fiber has a fiber Bragg grating, wherein the fiber Bragg grating has a periodic arrangement of sections along the direction of longitudinal extension of the optical fiber, wherein in each case, adjacent sections have different refractive indices, wherein the multiple photoacoustic absorbers are arranged in sections along the direction of longitudinal extension of the optical fiber on in each case one of the sections of the fiber Bragg grating, wherein the fiber Bragg grating is configured to filter the excitation light in the sections, wherein the filtered excitation light is configured to excite the multiple photoacoustic absorbers for modulated emission of the ultrasound.

5. A system for sensing a medical object, the system comprising:

the medical object for arrangement in an object under examination, the medical object comprising:

an optical fiber configured to contact at least one light source optically;

multiple photoacoustic absorbers that are arranged in sections along a direction of longitudinal extension of the optical fiber, along a periphery of the optical fiber, or along the direction of longitudinal extension of the optical fiber and along the periphery of the optical fiber, wherein the optical fiber comprises a sheathing, a portion of the sheathing being arranged between adjacent photoacoustic absorbers of the multiple photoacoustic absorbers, wherein the multiple photoacoustic absorbers are configured to be arranged at least in part in the object under examination, wherein the optical fiber is configured to conduct an excitation light emitted by the at least one light source to the multiple photoacoustic absorbers, and wherein the multiple photoacoustic absorbers are configured to be excited by the excitation light for photoacoustic emission of ultrasound;

a processing unit;

the at least one light source; and an ultrasound unit, wherein the at least one light source is configured to emit the excitation light, wherein the excitation light is configured to excite the multiple photoacoustic absorbers for the photoacoustic emission of the ultrasound, wherein the ultrasound unit is configured to be arranged extracorporeally on a surface of the object under examination, wherein the ultrasound unit is configured for detection of the ultrasound, wherein the processing unit is configured to determine a spatial progression of the medical object using the detected ultrasound, wherein in an operating state of the system:

the optical fiber optically contacts the at least one light source;

the multiple photoacoustic absorbers are arranged at least in part in the object under examination; and the ultrasound unit is arranged extracorporeally on the surface of the object under examination.

6. The system of claim 5, wherein the multiple photoacoustic absorbers have at least in part different excitation sensitivities for the photoacoustic emission of the ultrasound, wherein the processing unit is further configured to control the at least one light source for the emission of the excitation light such that the multiple photoacoustic absorbers are excited sequentially or simultaneously for the photoacoustic emission of the ultrasound, and wherein the excitation light is configured to excite the multiple photoacoustic absorbers selectively or non-selectively for the photoacoustic emission of the ultrasound.

7. The system of claim 6, wherein the processing unit is further configured to:

demodulate the detected ultrasound; and identify the multiple photoacoustic absorbers using the demodulated ultrasound.

8. The system of claim 5, wherein the optical fiber has a fiber Bragg grating, wherein the fiber Bragg grating has a periodic arrangement of sections along the direction of longitudinal extension of the optical fiber, wherein in each case, adjacent sections have different refractive indices, wherein the multiple photoacoustic absorbers are arranged in sections along the direction of longitudinal extension of the optical fiber on in each case one of the sections of the fiber Bragg grating, wherein the fiber Bragg grating is configured to filter the excitation light in the sections, wherein the filtered excitation light is configured to excite the multiple photoacoustic absorbers for modulated emission of the ultrasound, wherein the system further comprises a detector, wherein the optical fiber optically contacts the detector, wherein the detector is configured for detection of a portion of the excitation light reflected off the fiber Bragg grating, and wherein the processing unit is further configured to sense a deformation of the optical fiber using the detected excitation light.

9. The system of claim 5, wherein the ultrasound unit comprises multiple ultrasound transducers that are arranged in a line array, a matrix array, or the line array and the matrix array.

10. The system of claim 9, wherein the processing unit is further configured to:

receive a dataset having a mapping, a model, or the mapping and the model of the object under examination; and provide a superimposition dataset using the dataset and the detected ultrasound.

11. The system of claim 10, wherein the processing unit is further configured to:

determine a spatial positioning of one of the multiple photoacoustic absorbers using the detected ultrasound;

control the multiple ultrasound transducers based on the spatial positioning of the one photoacoustic absorber, such that an ultrasound field is emitted in two orthogonal planes, wherein in the operating state of the system, an axis of intersection of both the orthogonal planes runs through the one photoacoustic absorber, and wherein the multiple ultrasound transducers are further configured to detect a reflected portion of the ultrasound field; and generate the dataset having an intraoperative mapping of the object under examination using the detected ultrasound field.

12. The system of claim 10, further comprising a medical imaging device configured to record, provide, or record and provide the dataset.

13. The system of claim 10, wherein the processing unit is further configured to:
identify anatomical, geometric, or anatomical and geometrical features of the object under examination, of a further medical object arranged therein, or of a combination thereof in the dataset;
determine a spatial progression of the medical object with respect to the identified anatomical, geometric, or anatomical and geometrical features.

14. The system of claim 5, further comprising a movement apparatus for the robotic movement of the ultrasound unit,
wherein the movement apparatus is configured to position the ultrasound unit, and
wherein the processing unit is further configured to control the movement apparatus based on the detected ultrasound.

* * * * *